United States Patent
Deal

(10) Patent No.: US 8,690,756 B2
(45) Date of Patent: Apr. 8, 2014

(54) ADVANCING SYSTEM AND METHOD OF USE THEREOF

(75) Inventor: Stephen E. Deal, Charlotte, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 57 days.

(21) Appl. No.: 12/968,790

(22) Filed: Dec. 15, 2010

(65) Prior Publication Data

US 2011/0152616 A1 Jun. 23, 2011

Related U.S. Application Data

(60) Provisional application No. 61/288,259, filed on Dec. 18, 2009, provisional application No. 61/288,050, filed on Dec. 18, 2009, provisional application No. 61/288,060, filed on Dec. 18, 2009.

(51) Int. Cl.
*A61B 1/00* (2006.01)

(52) U.S. Cl.
USPC ........... 600/106; 600/104; 600/107; 600/114; 600/127

(58) Field of Classification Search
USPC ....................................................... 600/114
See application file for complete search history.

(56) References Cited

U.S. PATENT DOCUMENTS

| | | | |
|---|---|---|---|
| 6,048,620 A * | 4/2000 | Zhong ................. | 428/424.4 |
| 6,605,033 B1 | 8/2003 | Matsuno | |
| 6,689,051 B2 | 2/2004 | Nakada et al. | |
| 2001/0049509 A1 | 12/2001 | Sekine et al. | |
| 2002/0156344 A1 | 10/2002 | Pasricha et al. | |
| 2003/0088154 A1 | 5/2003 | Ishibiki et al. | |
| 2004/0267092 A1 | 12/2004 | Ishibiki | |
| 2005/0059890 A1 | 3/2005 | Deal et al. | |
| 2005/0222495 A1 | 10/2005 | Okada et al. | |
| 2005/0288549 A1 | 12/2005 | Mathis | |
| 2006/0069305 A1 * | 3/2006 | Couvillon et al. .......... | 600/117 |
| 2006/0258910 A1 | 11/2006 | Stefanchik et al. | |
| 2006/0264705 A1 | 11/2006 | Adams et al. | |
| 2007/0142709 A1 | 6/2007 | Martone et al. | |
| 2009/0259172 A1 | 10/2009 | Yamaoka et al. | |
| 2010/0113878 A1 | 5/2010 | Kawano | |

FOREIGN PATENT DOCUMENTS

| | | |
|---|---|---|
| DE | 20 2008 007 774 U1 | 9/2008 |
| EP | 1 284 120 A1 | 2/2003 |
| EP | 1 582 138 A2 | 10/2005 |
| EP | 1 721 567 A2 | 11/2006 |
| WO | WO 2007/091523 A1 | 8/2007 |

* cited by examiner

*Primary Examiner* — Matthew J Kasztejna
(74) *Attorney, Agent, or Firm* — Brinks Gilson & Lione

(57) ABSTRACT

A system is provided for advancing medical devices along an endoscope to a selected target anatomy in a patient. The advancing system includes a tether having a first portion disposed through a working channel of an endoscope and a second portion disposed external the endoscope. The advancing system may include a guiding device configured to advance a medical device beyond a distal portion of the endoscope to a selected target anatomy.

16 Claims, 15 Drawing Sheets

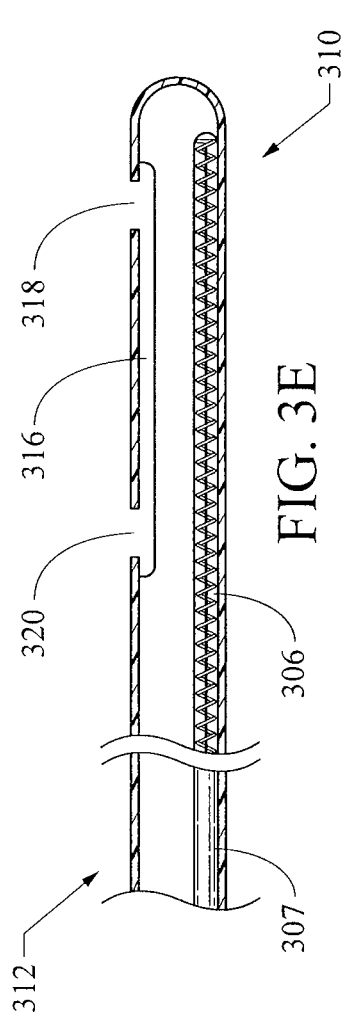
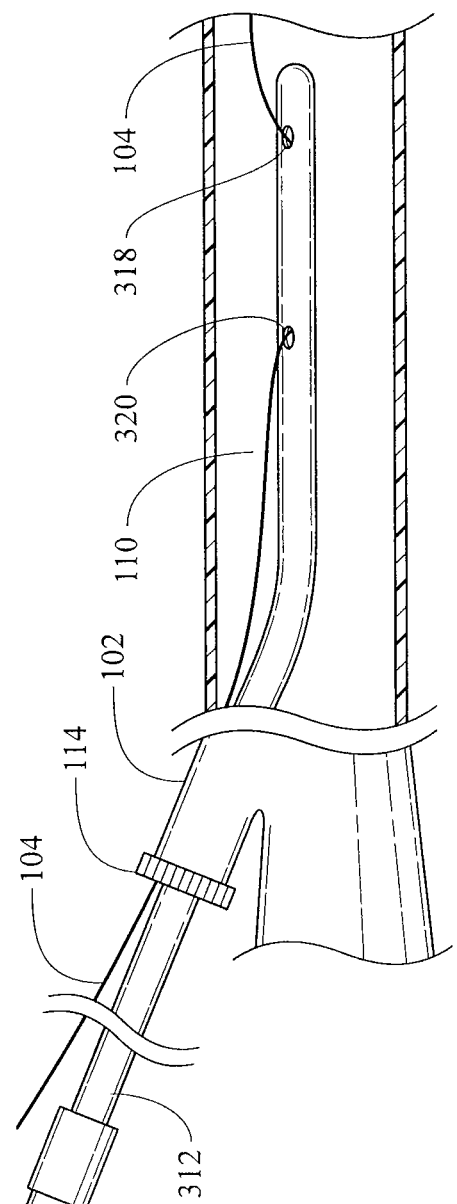

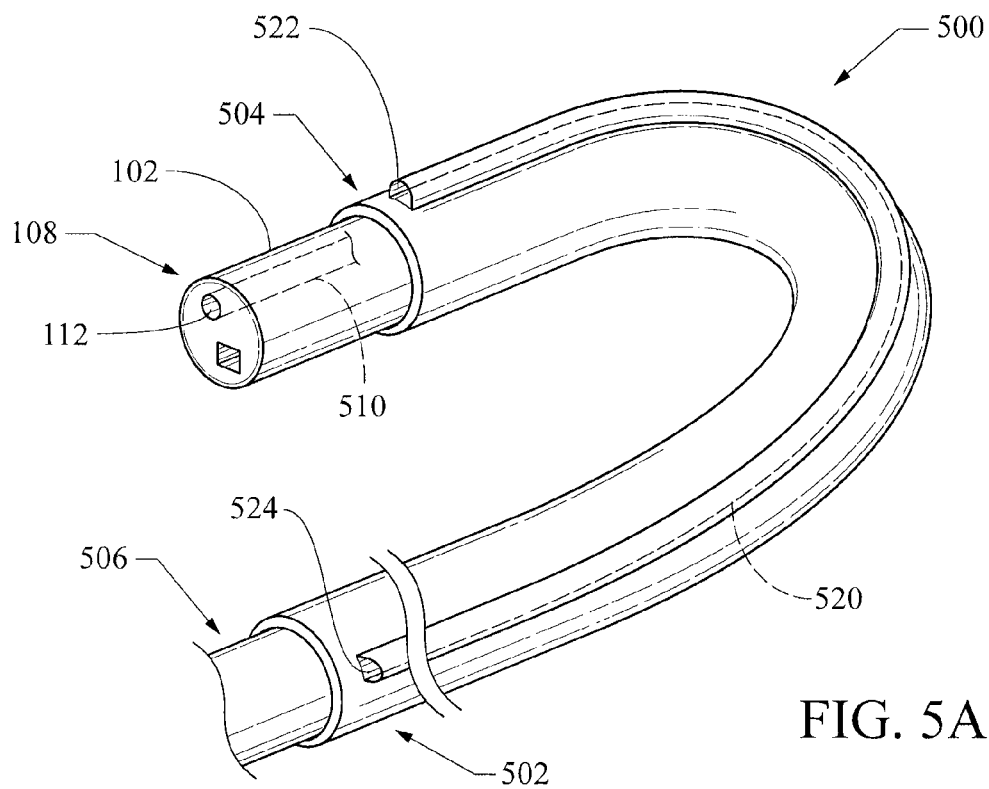
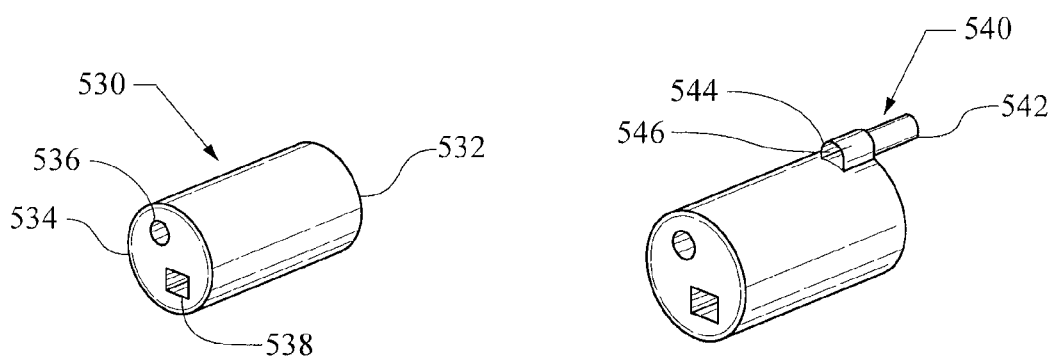 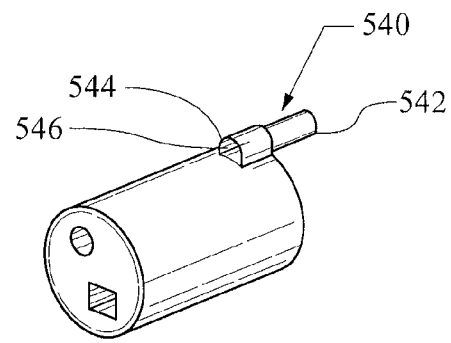
FIG. 5B  FIG. 5C
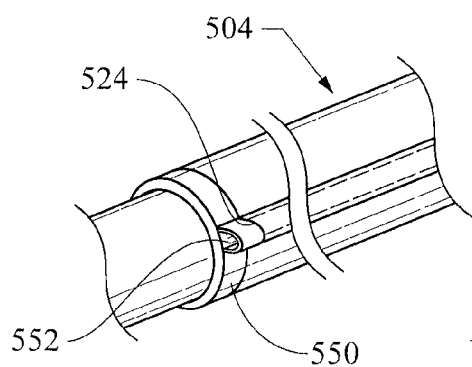
FIG. 5D

ADVANCING SYSTEM AND METHOD OF USE THEREOF

CROSS-REFERENCE TO RELATED APPLICATIONS

The present application claims the benefit of the following applications: U.S. Provisional Application No. 61/288,259, titled "Advancing System and Method of Use Thereof", filed Dec. 18, 2009, the entirety of which is hereby incorporated by reference; U.S. Provisional Application No. 61/288,050, titled "Endoscope Cap With Ramp", filed on Dec. 18, 2009, the entirety of which is hereby incorporated by reference; and U.S. Provisional Application No. 61/288,060, titled "Endoscope Sheath", filed Dec. 18, 2009, the entirety of which is hereby incorporated by reference.

TECHNICAL FIELD

The present invention relates to medical devices, and more particularly to an advancing system and method of use thereof for the delivery of medical devices alongside an endoscope to a selected target anatomy.

BACKGROUND OF THE INVENTION

Physicians use endoscopes during minimally invasive procedures to visualize the patient anatomy, diagnose various conditions, and deliver instrumentation to the treatment site. Devices are typically delivered via a working channel of the endoscope, which generally ranges from about 2.0 to 3.5 mm in diameter, and may be used to introduce catheters and other elongate devices, including forceps, scissors, brushes, snares, and baskets. Larger working channels of 5.0 mm in diameter are available in certain specialized endoscopes, and may be used to pass relatively large devices or provide capability for improved aspiration or decompression. Some devices, however, are simply too large to pass through available endoscopes. Moreover, the specialized endoscopes with larger working channels can be expensive, as well as difficult to intubate due to increased rigidity and outer diameter.

Devices too large for the endoscope working channel must be introduced through an alternate, and often more invasive procedure, such as laparoscopy or open surgery. Laparoscopic surgery involves creating 0.5-1.5 cm incisions in a patient's abdominal wall so that a laparoscope and other instruments can be introduced into the abdominal and pelvic cavities. Open surgery generally involves creating one or more long incisions in a patient, followed by extensive muscle stripping, prolonged retraction of tissues, denervation and devascularization of tissue. While effective at introducing larger devices, laparoscopic and open surgical procedures can increase the risk of complications and trauma to the patient, as well as extend recovery time and hospital stays.

What is needed are devices and methods for endoscopic introduction of medical devices too large for the endoscope working channel without necessitating the use of invasive procedures. Specifically, devices and methods are needed for introduction of medical devices alongside and external to an endoscope.

SUMMARY

Disclosed herein are devices and methods for introducing medical devices into the anatomy of a patient, and more particularly, for advancing a medical device along the exterior of an endoscope to a selected target anatomy. In general, the advancing system includes a tether for advancing devices alongside an endoscope. The advancing system may further include a guiding device for advancing devices beyond a distal portion of the endoscope. A device may be coupled to the tether and thereafter advanced to the distal end of the endoscope, and in some embodiments, to the distal end of the guiding device, preferably into a selected target anatomy.

In one aspect, a system is provided for advancing medical devices to a selected target anatomy in a patient. In one embodiment, the advancing system is adapted for use with an endoscope having a proximal portion, a distal portion, a working channel extending from the proximal portion to the distal portion, an aperture disposed at the distal portion and in communication with the working channel, and a port disposed at the proximal portion and in communication with the working channel. The advancing system includes a tether extending external the endoscope from the proximal portion to the distal portion to the aperture and extending from the aperture through the working channel to and out of the port.

In another embodiment, the advancing system includes a guiding device including an elongate shaft having a proximal portion and a distal portion, a fulcrum disposed at the distal portion and configured to receive a tether therethrough, a variable stiffness cable disposed in the elongate shaft, and an actuator disposed proximal to the proximal portion. The variable stiffness cable includes a helical spring extending from the proximal portion to the distal portion of the elongate shaft, and a wire extending through the spring. Preferably, the wire is operatively connected to the spring at the distal portion. The actuator is operatively connected to the wire.

In another aspect, a method is provided for advancing a medical device to a selected target anatomy in a patient. In one embodiment, the method includes advancing an endoscope to a selected target anatomy, coupling a medical device to a tether, and advancing the medical device along the endoscope using the tether. The endoscope includes a proximal portion, a distal portion, a working channel extending from the proximal portion to the distal portion, an aperture disposed at the distal portion and in communication with the working channel, and a port disposed at the proximal portion and in communication with the working channel. Initially, the tether extends external the endoscope from the proximal portion to the distal portion to the aperture and extends from the aperture through the working channel to and out of the port. The coupled medical device may be advanced along the endoscope from the proximal portion to the distal portion by pulling the tether out through the port.

In another embodiment, the method may include advancing a wire guide through the working channel to the aperture, and thereafter to a target anatomy beyond the distal portion of the endoscope. A guiding device may be advanced through the working channel to the aperture, and thereafter to the target anatomy beyond the distal portion of the endoscope. A medical device may be advanced along the guiding device to the target anatomy.

Other systems, methods, features and advantages will be apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The system may be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 3E-3F depict an alternative embodiment of guiding device 300.

FIG. 5A depicts endoscope sheath 500.

FIGS. 5B-5C depict cap member 530.

FIG. 5D depicts coupling member 550 coupled to lumen 520.

DEFINITIONS

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The term "biocompatible," as used herein, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived or escalating biological reaction or response. Such a response is distinguished from a mild, transient inflammation which typically accompanies surgery or implantation of foreign objects into a living organism.

The term "distal," as used herein, refers to a direction that is generally towards a target site within a patient's anatomy during a medical procedure.

The term "proximal," as used herein, refers to a direction that is generally towards a physician during a medical procedure.

The term "structure," as used herein, refers to any narrowing of a bodily lumen in relation to an adjacent lumen portion.

DETAILED DESCRIPTION

Figure 1A:
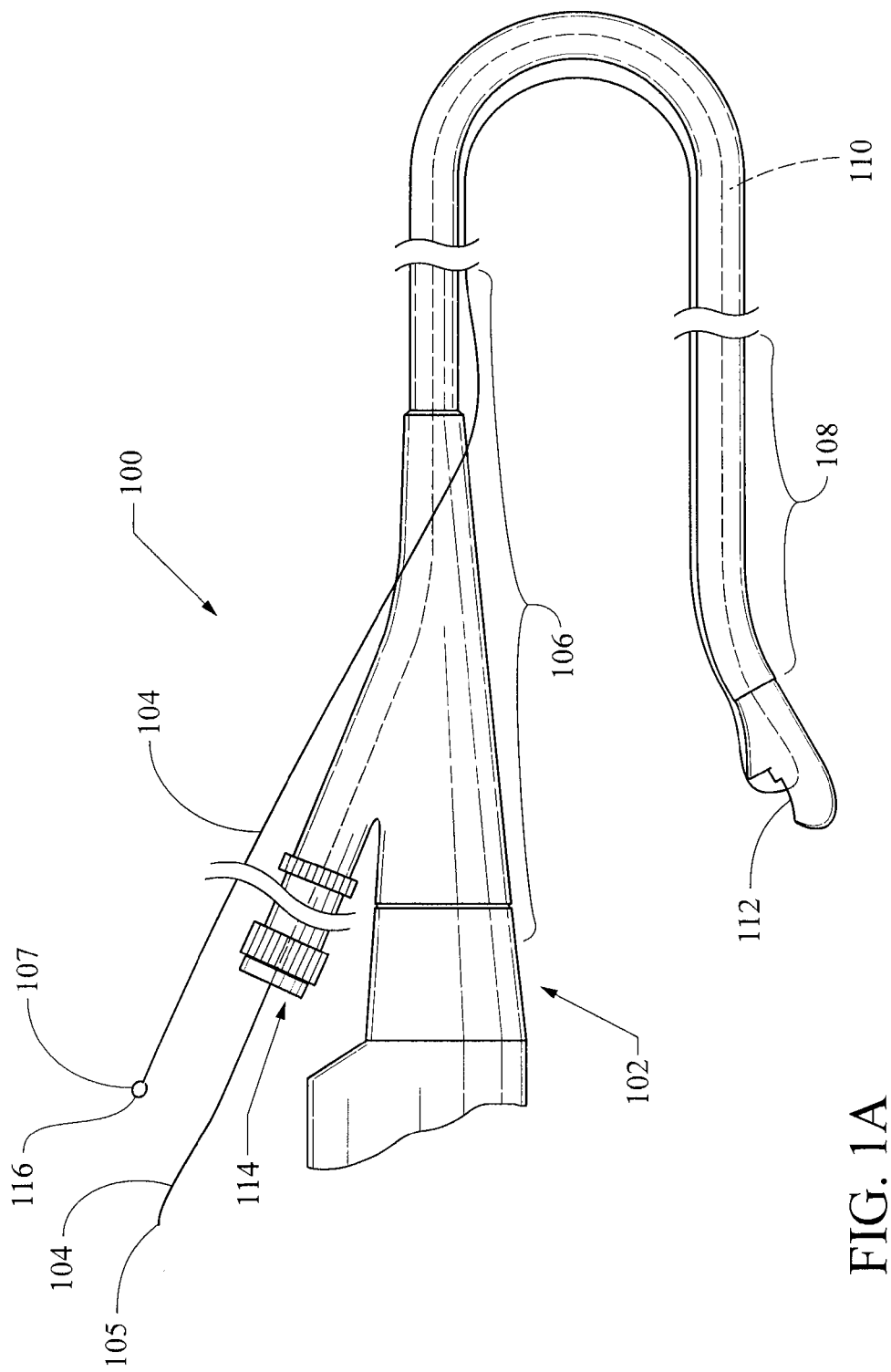
FIG. 1A depicts advancing system 100.

FIG. 1A depicts advancing system 100 including a tether 104. The advancing system is adapted for use with an endoscope 102. Endoscope 102 has a proximal portion 106, a distal portion 108, and a working channel 110 extending from the proximal portion to the distal portion. The working channel connects to an aperture 112 disposed at the distal portion. Tether 104 extends externally alongside the endoscope from the proximal portion 106 to the distal portion 108 and enters working channel 110 via aperture 112. The tether extends back through the working channel to proximal portion 106 and exits at port 114. The tether includes a first end 105 and a second end 107. The tether may include a coupling element 116, preferably located at second end 107. The coupling element may be attached to or integrally formed with tether 104. The coupling element may be attached to the tether by glue, adhesive, or suture, for example.

Figure 1B:
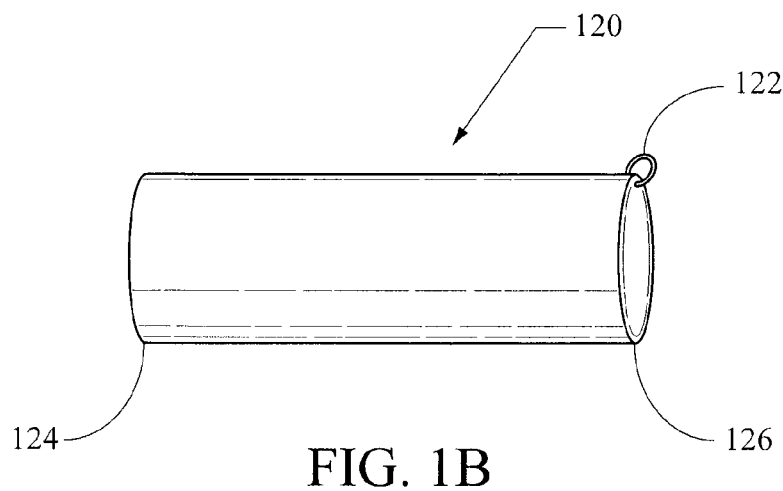
FIG. 1B depicts device 120.

FIG. 1B depicts a device 120 that may be delivered to a selected target anatomy. Device 120 is intended to be a generic representation of any device that may be delivered by the presently disclosed advancing system. Device 120 may be a device adapted to provide therapy or diagnosis to the selected target anatomy, or alternatively, a device configured to deliver another therapeutic or diagnostic device to the selected target anatomy. Device 120 may be, for example, a nasoenteric tube, a J portion of a PEG-J tube, a colon decompression tube, a biliary stent, a delivery catheter, an overtube, an introducer sheath, or another device. Device 120 includes a proximal end 124, a distal end 126, and may have a coupling element 122 complimentary to and configured to couple with coupling element 116. Alternatively, coupling element 122 may be configured to attach directly to tether 104. As will be explained in greater detail below, once endoscope 102 has reached a selected target anatomy and device 120 has been coupled to the tether, the device may be advanced to the distal portion of the endoscope by pulling the tether back through working channel 110 from port 114. Preferably, device 120 can be pushed from its proximal end 124 while the tether is used to pull from its distal end 126.

Tether 104 may be a strap, a wire, a suture, a thread, or any other device capable of functioning as a tether suitable for the intended use. Preferably, the tether is configured to bend without kinking. In cases where additional instruments will be introduced through the endoscope working channel or where the working channel will be used to provide aspiration or decompression, preferably the tether occupies minimal space therein and does not substantially interfere with the procedure. In one embodiment, the tether may be a wire having a 0.035 millimeter diameter, and can be used with an endoscope having a working channel diameter of 4.8 millimeters, for example. In another embodiment, the tether may be a flexible strap, such as a nylon strap, configured to conform to an inner surface of the endoscope working channel. The tether may be fabricated from a variety of biocompatible materials, including metal alloys and polymeric materials. Suitable polymeric materials include, for example, nylon, polyester, polyethylene, ultra-high molecular weight polyethylene, and polypropylene. Suitable metal alloys include, for example, nickel-titanium alloys. The tether can be coated with one or more materials. Preferably, at least a portion of the tether is coated with a hydrophilic or other lubricious material that can facilitate advancement of the tether through the anatomy of the patient. The tether may be coated with, for example, SLIP-COAT® Biopolymer, STS Biopolymers, Inc., Henrietta, N.Y.

The coupling elements 116 and 122 may include any suitable structures configured to temporarily couple two medical devices. For example, the coupling elements may include a closed loop structure as depicted in FIGS. 1A-1B. The coupling elements may include releasable or breakable sutures, temporary or dissolvable bonds or adhesives, magnets, or a combination thereof. The coupling elements may include a biocompatible ball which is crimped, glued, or otherwise designed to slide off or break apart with the application of sufficient amount of pull force (e.g., 3 pounds), and can thereafter be safely passed through the gastrointestinal system or be absorbed thereby. Optionally, device 120 may be coupled directly to the tether, with for example, breakable or dissolvable sutures.

Figure 2A:
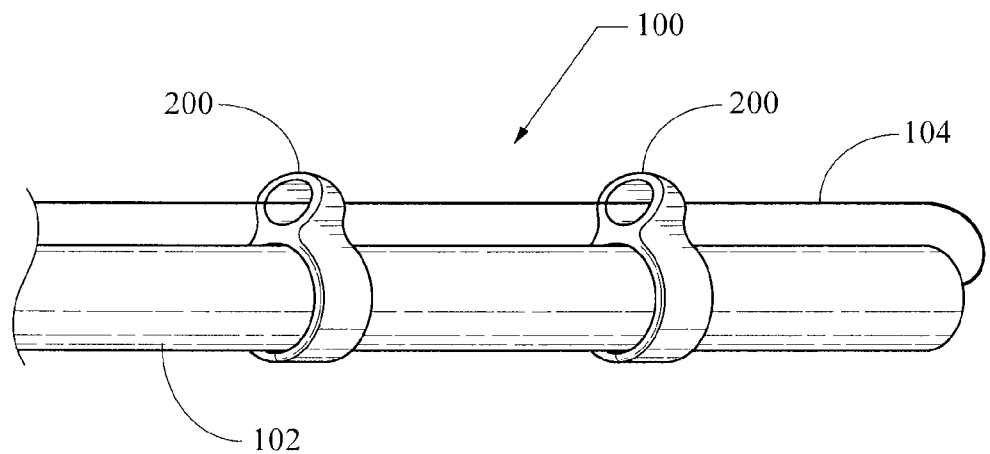
FIGS. 2A-2B depict guide rings 200 disposed on endoscope 102.
Figure 2B:
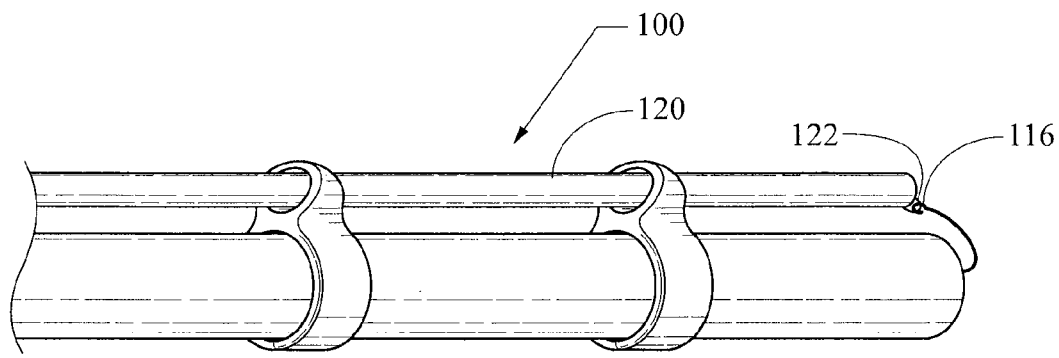
Figure 2C:
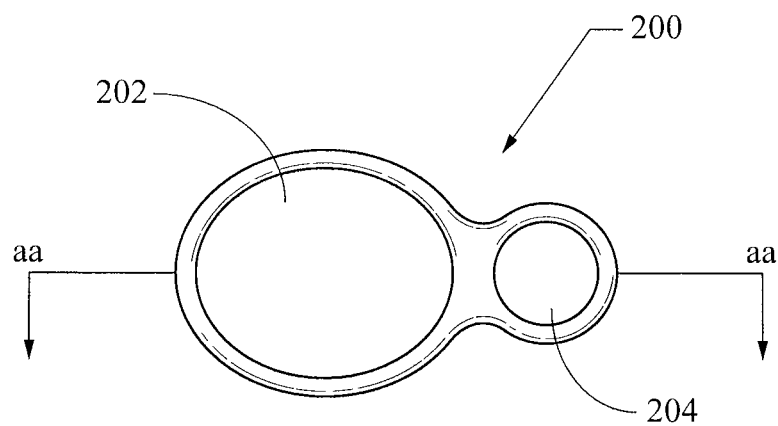
FIG. 2C depicts a perspective view of a guide ring 200.
Figure 2D:
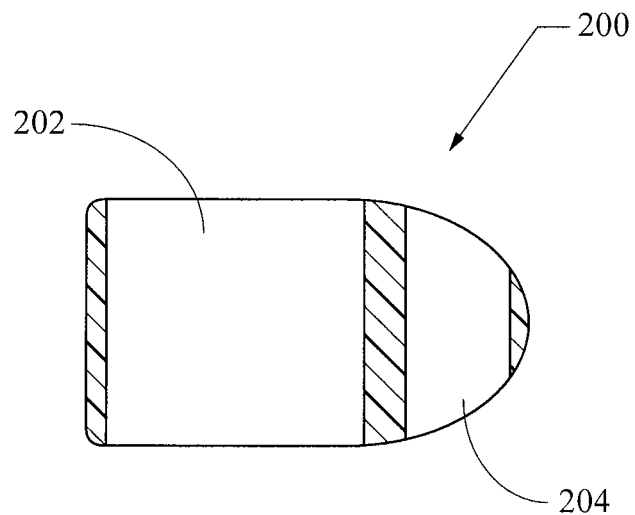
FIG. 2D depicts a cross-sectional view of guide ring 200 taken along line aa of FIG. 2C.

FIGS. 2A-2B depict guide rings 200 disposed along an external surface of endoscope 102. Preferably, the tether passes through the guide rings as it moves along the endoscope, tracking closely therewith. Maintaining the tether within the rings may help minimize mucosal trauma caused by the tether or device 120, and additionally, may prevent the tether or device 120 from interfering with the endoscope visualization devices (e.g., its camera, CCD, or fiber-optic element). As device 120 is delivered to a distal portion of the endoscope, it may be configured to slide into position within the guide rings, as shown in FIG. 2B. Device 120 may then bend and move in concert with the distal portion of the endoscope. The guide rings may be configured to allow device 120 to pass completely therethrough. FIG. 2C shows guide ring 200 having a lumen 202 for the endoscope and a lumen 204 for device 120. In general, the guide rings are annular or penannular shaped and preferably have a minimally traumatic profile wherein the rings include rounded edges, such as that depicted in the top, cross-sectional view of FIG. 2D. The guide rings may be integral with the endoscope, attached by a biocompatible adhesive, adapted to snap onto the endoscope, or a combination thereof.

FIGS. 3A-3G depict a guiding device 300 that can be used to advance devices beyond the distal portion of the endoscope. Guiding device 300 includes a flexible or semi-flexible elongate member 302, a fulcrum 304, and a variable stiffness cable 306. The elongate member 302 includes a distal portion 310 and a proximal portion 312. The elongate member may have a range of lengths and diameters depending on the size of the working channel of the endoscope to be used and the procedure to be performed. In general, the length of elongate member 302 ranges from about 100 cm to about 300 cm. The cross-sectional diameter generally ranges from about 1 mm to about 3 mm, and is preferably configured for advancement through the working channel of the endoscope. The skilled artisan will appreciate that all dimensions provided herein are intended as examples only, and guiding devices having different dimensions may be substituted for a particular use.

Elongate member 302 includes a biocompatible material that encases variable stiffness cable 306, shielding it from direct exposure to the patient anatomy. The material may be, for example, expanded polytetrafluoroethylene, polytetrafluoroethylene, polyethylene, or polyurethane. In one exemplary embodiment, elongate member 302 may be fabricated by placing heat shrink tubing, such as heat shrink polytetrafluoroethylene tubing, over the variable stiffness cable 306 and thereafter heat shrinking the tubing in place. The elongate member may comprise one or more materials providing the member with properties of sufficient strength, flexibility, and resistance to compression in order to traverse tortuous areas of the anatomy. Such materials include nylon, polyether block amides, polyethylene terephthalate, polytetrafluoroethylene, polyetheretherketone, or combinations thereof. The skilled artisan will appreciate, however, that the elongate member may be constructed from other biocompatible materials as is known in the art to provide the desired properties.

Figure 3A:
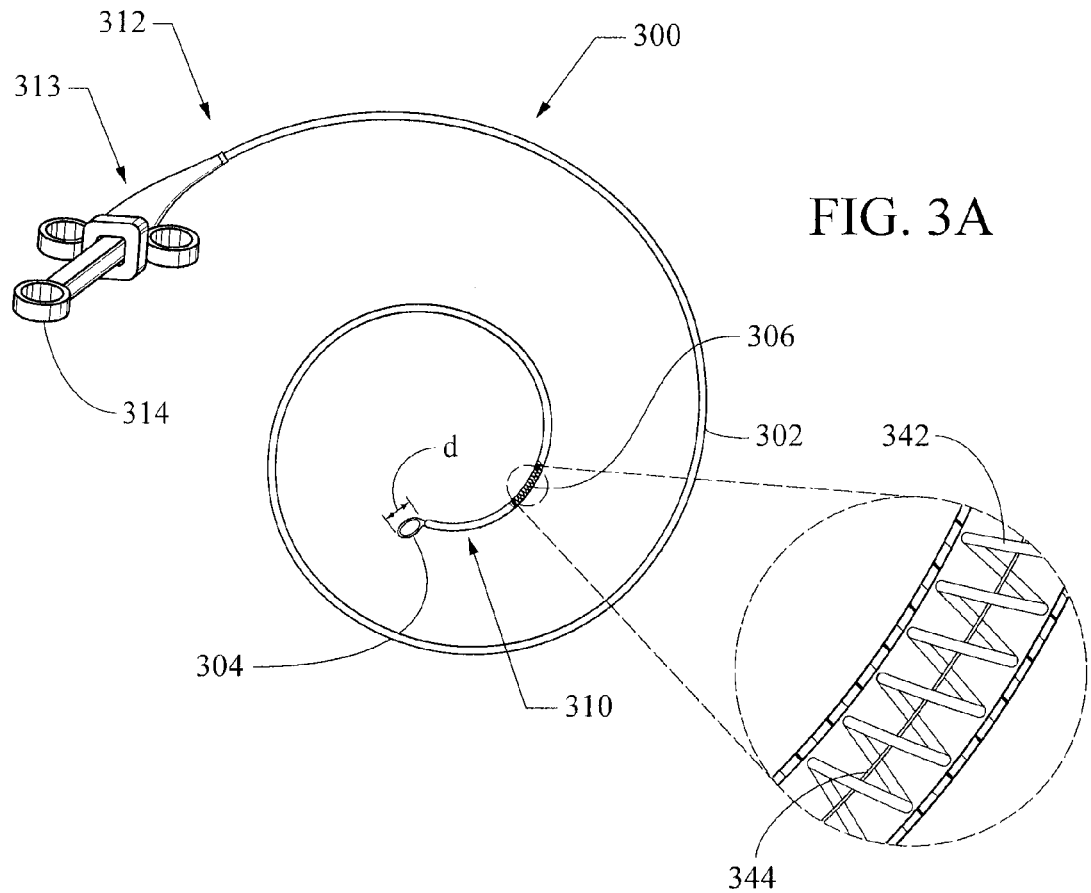
FIGS. 3A-3C depict guiding device 300.
Figure 3B:
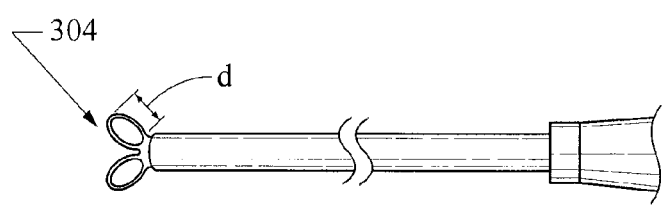
Figure 3C:
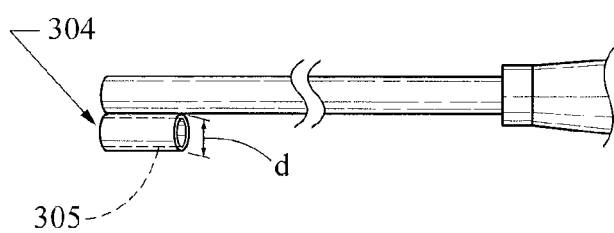

Fulcrum 304 is attached to or integrally formed with distal portion 310 of elongate member 302. The fulcrum may be any suitable structure configured to receive tether 104 and provide a point at which the tether can be advanced through or around. Fulcrum 304 may be, for example, a single loop structure (FIG. 3A), a double loop structure (FIG. 3B), or a cylindrical structure having a lumen 305 extending therethrough (FIG. 3C). The fulcrum has a diameter d preferably ranging from about 1 mm to about 3 mm. In some embodiments, the fulcrum may be constructed of wire, suture, or thread. In other embodiments, the fulcrum may be constructed of a more rigid material. In general, however, fulcrum 304 may comprise any material suitable for the intended use. The fulcrum may include, for example, polymeric materials such as nylon, and/or metallic materials such as nickel-titanium alloys.

Portions of the guiding device can be coated with one or more materials. Preferably, at least a portion of elongate member 302 is coated with a hydrophilic or other lubricious material. Hydrophilic or other lubricious coatings are known to facilitate advancement of devices through patient anatomy or introducer devices. In some embodiments, fulcrum 304 may be comprised of and/or coated with a material that facilitates smooth advancement of the tether therethrough. Preferred materials include polytetrafluoroethylene, ultra-high molecular weight polyethylene (UHMWPE), nylon, and polyoxymethylene.

Variable stiffness cable 306 is disposed through elongate member 302 and includes helical spring 342 extending from proximal portion 312 to distal portion 310 near fulcrum 304. The spring includes a small pitch between the adjacent turns. A wire 344, such as a stainless steel wire, extends through the central bore of spring 342 and is affixed to the distal end thereof. Alternatively, the wire and the spring may both be affixed to a distal tip. Wire 344 is operatively connected to a hand assembly 313 located proximal to proximal portion 312. Hand assembly 313 includes an actuator 314 that can be used to compress or decompress spring 342. For example, in some embodiments, retraction of the actuator in the proximal direction retracts wire 344. This retraction of the wire reduces the distance between the turns in spring 342, and thereby reduces the spring's flexibility. Additional examples of variable stiffness cables are disclosed in U.S. Pat. Nos. 4,215,703 and 3,854,473, the disclosures of which are herein incorporated by reference in their entirety.

Figure 3D:
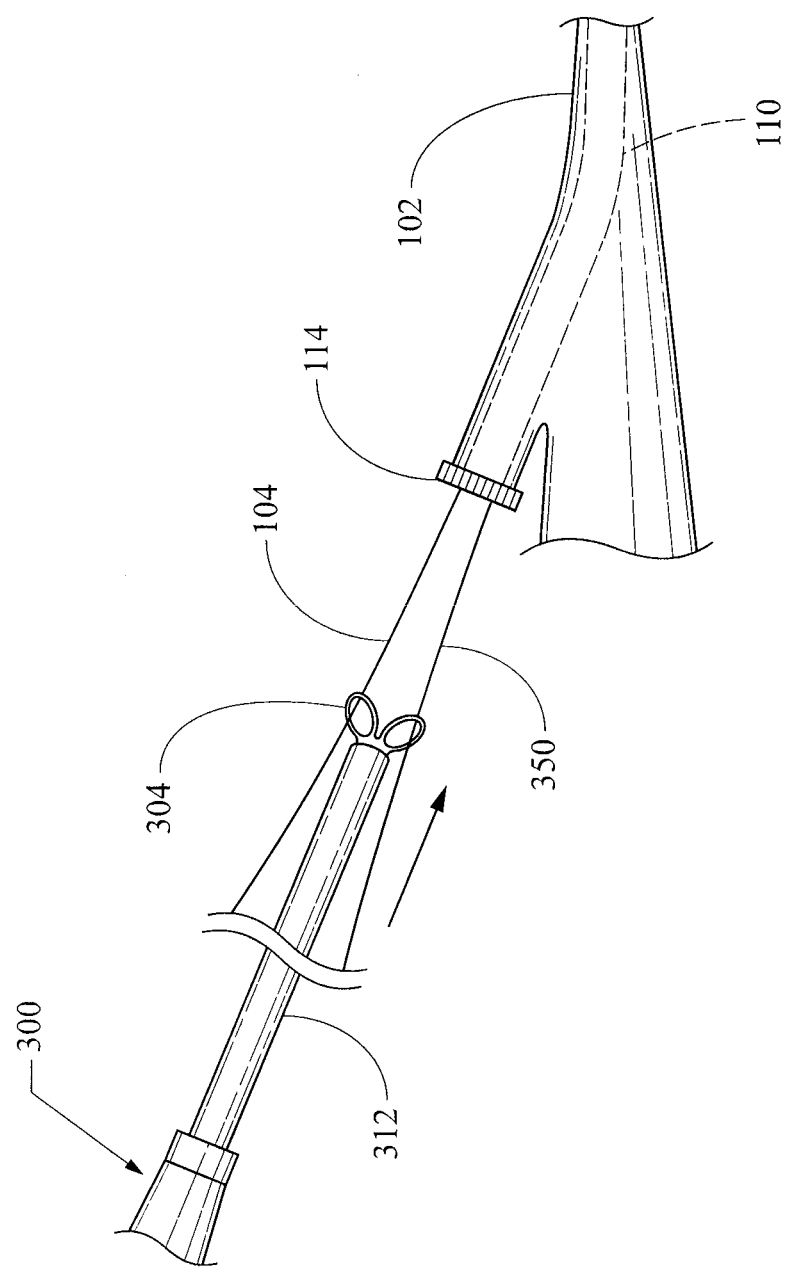
FIG. 3D depicts loading of guiding device 300 onto the tether and wire guide.

Guiding device 300 may be loaded onto tether 104 at the proximal portion of the endoscope by passing first end 105 of tether 104 through fulcrum 304. Preferably, the guiding device is also loaded onto the proximal end of a wire guide 350 that exits port 114 and has been used to cannulate the target anatomy. The tether and the wire guide may be passed, for example, through the double loop fulcrum 304, as depicted in FIG. 3D. The elongate member 302 can then be advanced into the working channel 110 via port 114. Thereafter, the elongate member may be advanced through the working channel, out aperture 112, and to a selected target anatomy beyond distal portion 108. In some embodiments, an endoscopic elevator apparatus may be used to aid in advancement of the elongate member into the selected target area. As the elongate member advances beyond the distal portion of the endoscope, preferably the tether becomes looped around the fulcrum and is advanced into the target anatomy.

In an alternative embodiment, elongate member 302 may include aperture 318 that serves as the fulcrum 304 (FIGS. 3E-3F). Aperture 318 is located on distal portion 310 and is in communication with a lumen 316 extending proximally to an aperture 320. The guiding device may be loaded onto tether 104 at the proximal portion of the endoscope using the "short wire technique." Specifically, first end 105 may be passed into aperture 318 to lumen 316, and then to and out of aperture 320. Thereafter, elongate member 302 may be advanced through working channel 110. As the elongate member advances beyond the distal portion of the endoscope, preferably the tether is pulled along therewith, the tether looping back from aperture 318. The guiding device can be loaded onto wire guide 350 according to the same procedure. The skilled artisan will appreciate, however, that the guiding device may be configured with apertures and lumens as appropriate so that the device can be loaded by either of the short wire technique or the long wire technique. Both techniques are disclosed in U.S. Patent Application Publication No. 2007/0167923, the disclosure of which is herein incorporated by reference in its entirety.

Figure 3G:
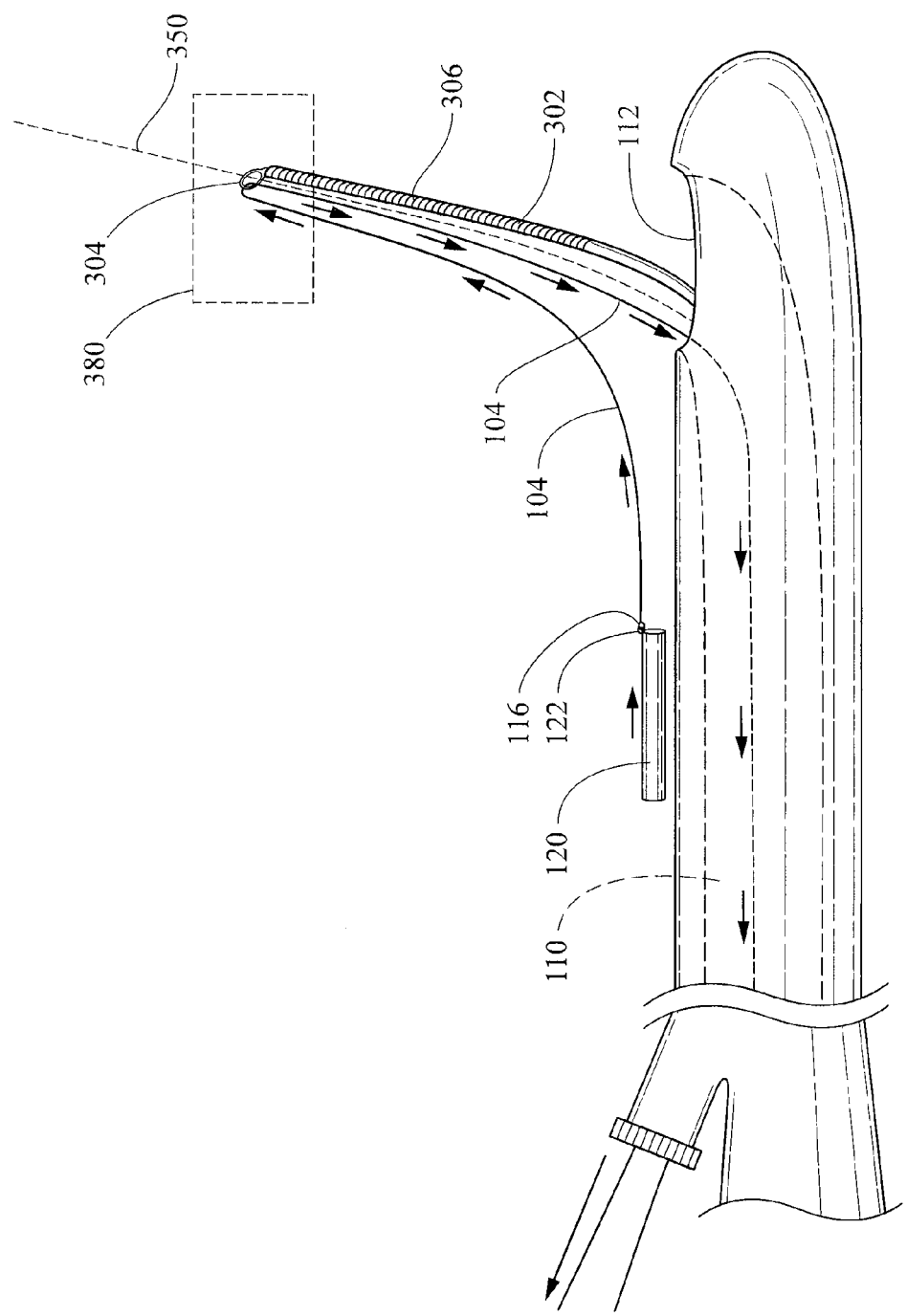
FIG. 3G depicts elongate member 302 advanced into a target anatomy 380.

Once distal portion 310 of elongate member 302 reaches a target anatomy 380, the variable stiffness cable 306 may be used to stiffen and anchor the elongate member in place (FIG. 3G). The tether can then be pulled back through working channel 110 from port 114, thereby advancing a coupled device 120 toward the target anatomy. Preferably, device 120 may be pulled at its distal end 126 with the tether while pushed at its proximal end 124. Pushing and pulling the device may reduce the incidence of trauma incurred by tissue surrounding the path of introduction, as well as facilitate smooth advancement. In some embodiments, device 120 may include a stiffening or reinforcing element in order to provide the device with sufficient rigidity for effective pushing.

During introduction of the endoscope and extension of the guiding device into the target anatomy, the tether can be held secure as needed. Preferably, the tether is long enough so that control can be maintained at both ends while the endoscope and guiding device are advanced to the target anatomy. In other words, preferably the tether is greater than two times the length of the endoscope. In embodiments using the guiding device, preferably the tether is greater than two times the additive length of the endoscope and the length of the portion of elongate member 302 that extends out of aperture 112 and to the target anatomy. The portion of tether exiting port 114 can be held secure at the port by, for example, a locking device (e.g., Fusion® Wire Guide Locking Device, Cook Endoscopy Inc., Winston-Salem, N.C.), or by holding the tether. Likewise, the other end of the tether, specifically the portion of tether running external along the endoscope to the proximal portion 106, can be held secure by a locking mechanism or similar device, or by holding the tether. As elongate member 302 or device 120 is advanced into the target anatomy, the tether can be unlocked as needed.

Figure 4A:
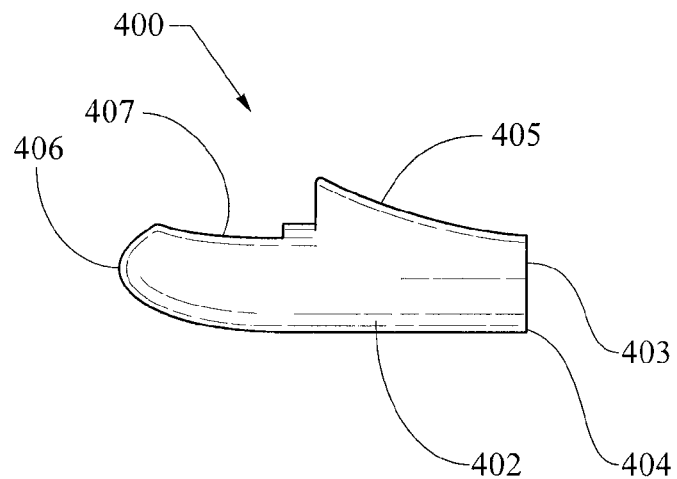
FIGS. 4A-4B depict endoscope cap 400 having a stationary ramp.
Figure 4B:
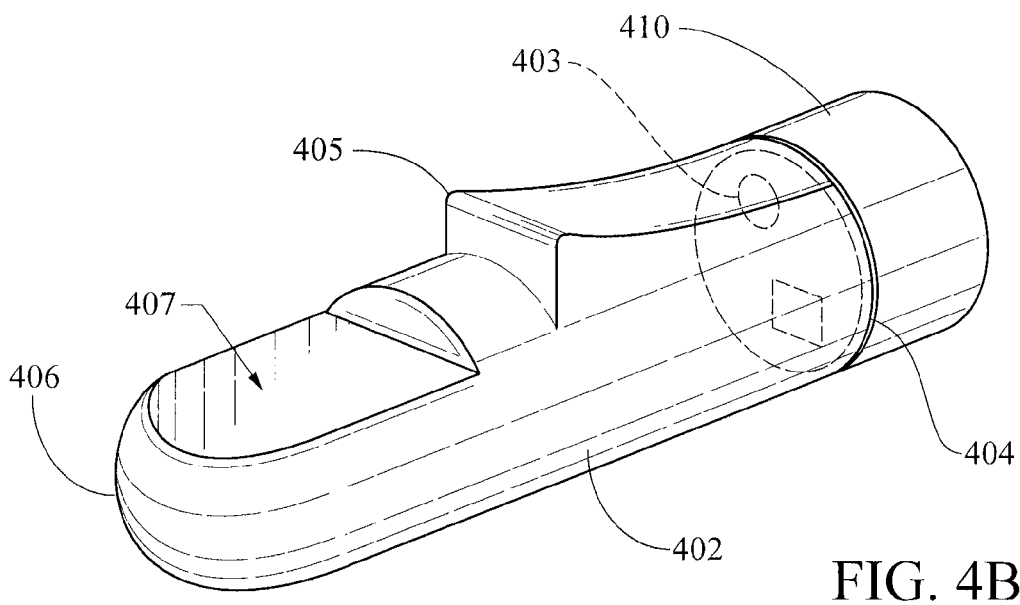

Optionally, an endoscope cap including a ramp may be used with the advancing system to aid in delivery of device 120. As device 120 reaches a distal portion of endoscope 102, the cap may be used to deflect the device into the target anatomy, such as the pancreatic duct. FIGS. 4A-4B depict an endoscope cap 400 configured for a duodenoscope. The cap includes a body 402 having a proximal end 404 and a distal end 406. The proximal end 404 includes an aperture 403 configured to receive a distal portion of the endoscope. Cap 400 further includes a ramp 405 that can be used to deflect medical devices toward a selected target anatomy. Cap 400 further includes a side aperture 407 configured to accommodate the endoscope's visualization devices (e.g., camera, CCD, or fiber-optic element) and working channel(s).

Body 402 and ramp 405 may be constructed of rigid material(s). In some embodiments, all or a portion of the body and the ramp may be generally transparent. For example, the body may be constructed of a clear polycarbonate polymer. Alternatively, it may be constructed of another clear, translucent, or opaque polymer such as polyurethane, acrylic, or nylon. Body 402 may be dimensioned such that its outer diameter (with exception to the ramp) is about the same as the outer diameter of the endoscope on which cap 400 is to be used. For example, body 402 may have an outer diameter of about 8.5 mm to about 12 mm for use with endoscopes having those outer diameters. The skilled artisan will appreciate that body 402 may be dimensioned appropriately for use with endoscopes having greater or lesser diameters, and it may also have a cross-section configured for use with a similarly-shaped endoscope.

In some embodiments, the cap may include an engagement portion 410 configured to secure the cap to the endoscope. The engagement portion may be integral with or attached to proximal end 404 of the cap. The engagement portion, which preferably extends proximally from body 402 may be constructed from a flexible material that provides a frictional inner diameter surface. For example, the engagement portion may be constructed of a clear polyurethane that is molded to body 402. In other embodiments, it may be constructed from, for example, silicone or another soft polymer that will provide an ability to mount and frictionally (but removably) attach cap 400 to the endoscope.

In an alternative embodiment, the entire cap, including an engagement portion, may be constructed of a rigid material. The cap may include any suitable structure or materials configured to attach the cap to the endoscope. For example, the cap may include an adhesive, magnets, a threaded surface, a detent structure, or other structures and materials known in the art. In another alternative embodiment, the endoscope may include a structure near its distal end for engaging the cap, such as for example, complementary threaded surfaces, interlocking tabs/slots, or another structure configured to attach the cap to the endoscope. Illustrative examples of such engagement portions can be found in U.S. Patent Application Publication No. 2009/0105539, the disclosure of which is herein incorporated by reference in its entirety.

Figure 4C:
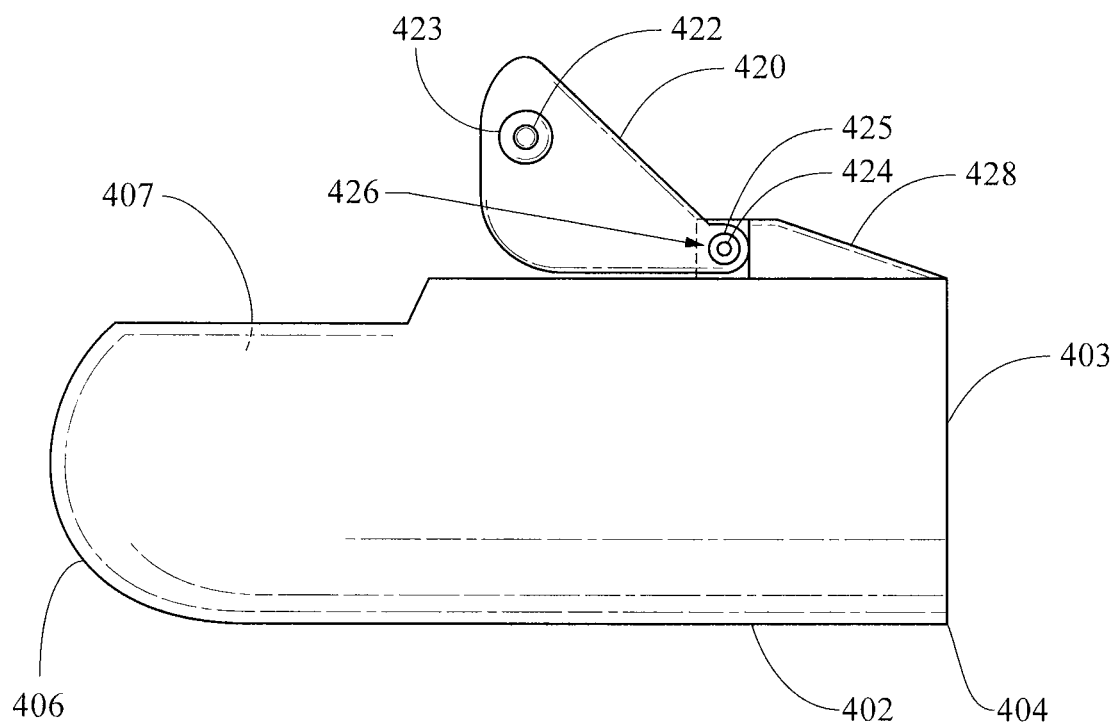
FIGS. 4C-4E depict endoscope cap 400 having a pivotable ramp.
Figure 4D:
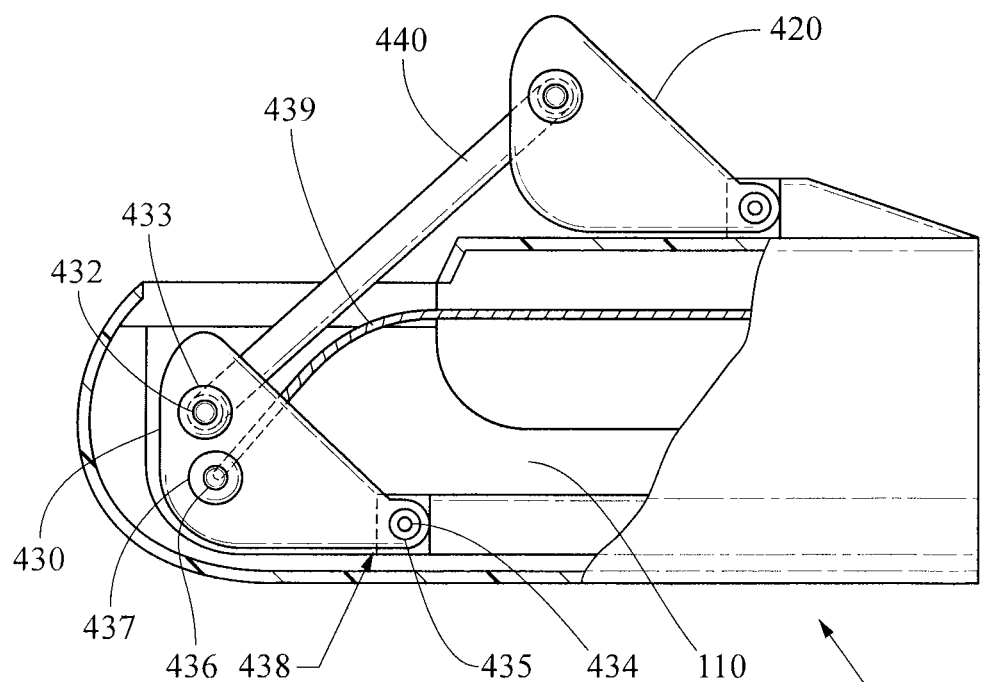
Figure 4E:
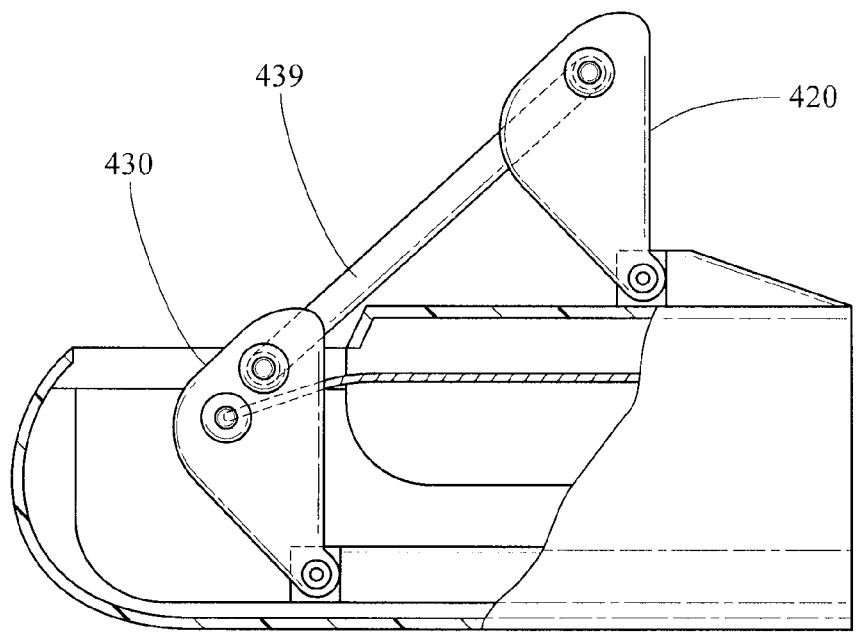

FIGS. 4C-4E show another embodiment of cap 400 including a ramp 420 pivotally attached to the cap. The ramp includes transverse passageways 422 and 424. Optionally, each respective passageway may include metal sleeves 423 and 425. Ramp 420 is pivotally attached to the cap by a ramp turning support 426, part of which is partially disposed through transverse passageway 424. The cap may further include a stationary ramp 428 configured to provide smooth transition from the external surface of the endoscope to the ramp 420.

FIGS. 4D-4E depict the cap of FIG. 4C disposed on the distal end of endoscope 102. The endoscope includes an elevator 430 that may be detachedly connected to ramp 420 by a connecting bar 440. Elevator 430 includes transverse passageways 432, 434, and 436. Optionally, each respective passageway may include metal sleeves 433, 435 and 437. The elevator is pivotally attached to the endoscope by an elevator turning support 438, part of which is partially disposed through transverse passageway 434. An elevator wire 439 is connected at one end to elevator 430, and operatively connected at the other end to a control system located at the proximal portion of the endoscope. Manipulation of the control system moves the elevator wire relative to the endoscope. As the elevator wire is retracted toward the proximal portion of the endoscope, elevator 430 moves about the elevator turning support 438. The elevator may be used to deflect devices delivered through working channel 110 into a desired direction. For example, the elevator may be used to deflect wire guide 350 and guiding device 300 into the biliary system of a patient. A more detailed description of a similar endoscopic elevator apparatus can be found in U.S. Patent Application Publication No. 2007/0208219, the disclosure of which is hereby incorporated by reference in its entirety.

Figure 4F:
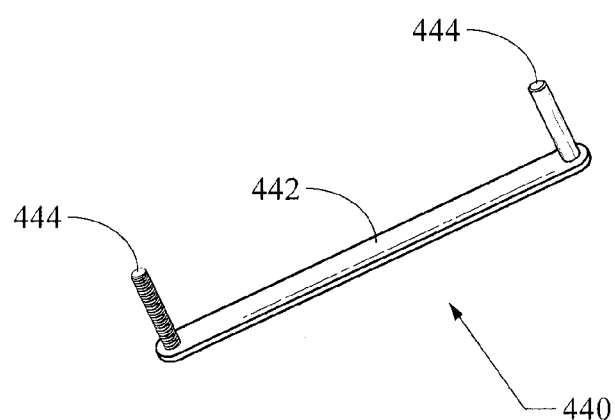
FIG. 4F depicts connecting bar 440.

The connecting bar 440 includes an elongate member 442 and two attachment elements 444 (FIG. 4F). The connecting bar may be attached to elevator 430 and ramp 420 by inserting the attachment elements into transverse passageways 422 and 432. Attachment elements 444 may be cylindrically shaped structures attached to or integral with elongate member 442. Preferably, the attachment elements can engage in axial motion about their respective central axes. For example, the attachment elements may include an outer portion and an inner portion separated by bearings that allow the outer portion to rotate about the attachment element central axis. The attachment elements may include any suitable structural elements necessary to engage the elevator 430 and ramp 420. For example, attachment elements 444 and transverse passageways 422 and 432 may have complimentary threaded surfaces.

When elevator 430 and ramp 420 are attached by connecting bar 440, actuation of elevator 430 causes actuation of ramp 420. FIG. 4D shows elevator 430 and ramp 420 in a first configuration wherein elevator wire 439 is not retracted toward the proximal portion of the endoscope. FIG. 4E shows elevator 430 and ramp 420 in a second configuration wherein the elevator wire is retracted toward the proximal portion of the endoscope. As a device is advanced down alongside the endoscope, ramp 420 may be actuated from the first configuration to the second configuration to deflect the delivered device toward the selected target anatomy. The skilled artisan will appreciate that in some cases, ramp 420 need not be fully actuated from the first configuration to the second configuration, but rather may be actuated to a configuration as needed for the particular procedure.

Optionally, an endoscope sheath may be used with the advancing system to facilitate delivery of devices alongside the endoscope. FIG. 5A shows a sheath 500 having a proximal portion 502 and a distal portion 504. The sheath includes a first lumen 510 for an endoscope and a second lumen 520 for devices delivered alongside the endoscope. Lumen 520 extends from the proximal portion 502 to the distal portion 504 and has distally located aperture 522, and proximally located aperture 524. As depicted, endoscope 102 is disposed through lumen 510, the sheath extending over the endoscope's proximal portion 106 to its distal portion 108. The sheath may have a range of widths and lengths depending on the size of the endoscope to be used. In general, the sheath length ranges from about 100 cm to about 200 cm; and the sheath has a wall thickness of between about 0.1 mm to about 8 mm. In one embodiment, the sheath may be constructed from expanded polytetrafluoroethylene (ePTFE).

Optionally, the sheath may include a cap member 530 that attaches to the distal end of endoscope 102, depicted as an end viewing endoscope in FIG. 5A. The cap member may be a tubular structure having a proximal end 532 and a distal end 534. The proximal end 532 may be configured to engage the distal end of the sheath. Alternatively, the cap may be fixedly attached to the distal end of the sheath. The distal end 534 may have openings 536 and 538 configured to align with aperture 112 and the endoscope visualization device, respectively.

Cap member 530 may further include a coupling member 540 configured to engage lumen 520 at aperture 522 (FIG. 5C). Coupling member 540 may be configured to frictionally engage the inner surface of lumen 520 near aperture 522. The coupling member includes a proximal end 542, a distal end 544, and a lumen 546 extending therethrough from the proximal end 542 to the distal end 544. Preferably, device 120 may be advanced along the endoscope through sheath lumen 520, enter lumen 546, and thereafter exit into the patient anatomy.

Optionally, the sheath may include another coupling member 550 coupled or configured to couple with lumen 520 at aperture 524 (FIG. 5D). Coupling member 550 includes a lumen 552 through which a device may be inserted and thereafter advanced through lumen 520 toward the distal portion of the endoscope. Coupling member 550 may be attachable or integral with the proximal end of the sheath. Preferably coupling member 550 is configured to releasably attach to the endoscope. For example, the coupling member may be configured to frictionally engage a proximal portion of the endoscope and/or the sheath.

FIGS. 6A-6G demonstrate a method by which a medical device can be introduced alongside the endoscope to a selected target anatomy. In one exemplary embodiment, the advancing system can be used with Endoscopic Retrograde Cholangiopancreatography (ERCP). ERCP involves inserting a duodenoscope into a patient's mouth and through the esophagus, stomach, and duodenum until it reaches the area where the ducts of the biliary tree and the pancreas open into the duodenum. Devices delivered through the endoscope's working channel may then traverse the Papilla of Vater for access to the ductal system. Therein, these devices can be used to perform diagnostic and therapeutic procedures. Examples of such devices include wire guides, baskets, snares, stents, extraction balloons, introducer brushes, catheters, and baby endoscopes usually of 0.8 mm to 4 mm in diameter.

One ERCP procedure includes delivery of a plastic biliary stent into an area of the bile or pancreatic duct where a stricture is blocking drainage of fluid. The blockage may be caused by a tumor in the bile or pancreatic duct. Typically, by the time symptoms appear in the patient, the tumor is at an advanced stage and is deemed inoperable. As a result, management of the cancer usually focuses on palliation of the symptoms. As an alternative to surgical bypass procedures for palliation, a stent may be delivered by ERCP and positioned through the obstructed area so as to maintain a pathway for fluid to flow across. However, the maximum diameter of a plastic biliary stent generally depends on the diameter of the endoscope's working channel. As a result, in some instances multiple stents must be placed within the stricture to allow for sufficient drainage. Using the presently disclosed advancing system, plastic biliary stents having diameters larger than the endoscope's working channel can be delivered to the bile or pancreatic ducts. These larger tubes may facilitate more efficient drainage of the duct and may be less prone to clogging compared to their smaller counterparts.

FIGS. 6A-6G illustrate delivery of a large plastic biliary stent 610 into the common bile duct. The procedure begins with endoscope 102 and tether 104 in place as depicted in FIG. 1. The endoscope may then be advanced into the patient and positioned in the duodenum 602 to allow viewing of the Sphincter of Oddi and the Papilla of Vater 604, which lie at the opening to the common bile duct 606 and the pancreatic duct. Next, the wire guide 350 may be extended out of aperture 112, through the Ampulla of Vater and into the ductal system (FIG.

Figure 6A:
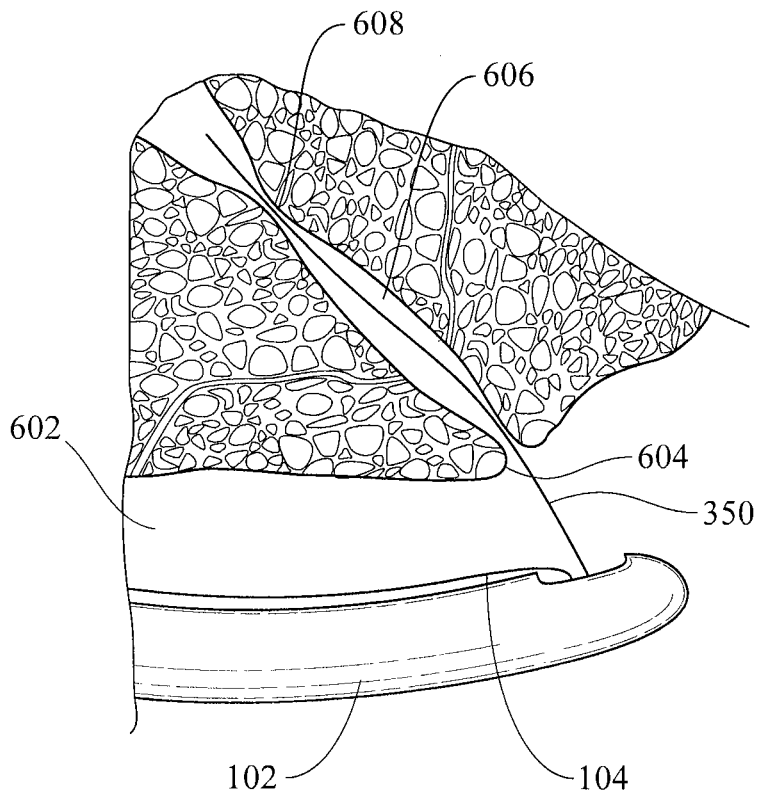
FIGS. 6A-6G depict delivery of a large plastic biliary stent into the common bile duct using advancing system 100.
Figure 6B:
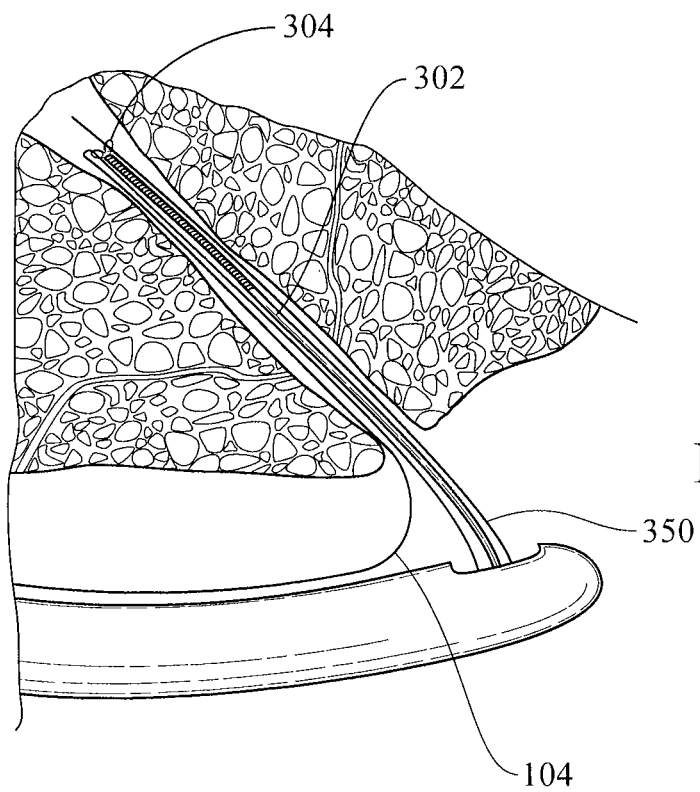

6A). Preferably, the wire guide is advanced past the stricture 608. A dilator catheter may be used as needed to facilitate cannulation of the duct. A more detailed description of cannulation of the common bile duct with the assistance of a dilator catheter is disclosed in U.S. Patent Application Publication No. 2005/0059890, the disclosure of which is herein incorporated by reference in its entirety. The guiding device 300 can be loaded over the wire guide and the tether 104 at the proximal portion of the endoscope. Elongate member 302 of the guiding device may be advanced through the endoscope's working channel and thereafter extended out of aperture 112 and into the ductal system, all the while advancing over the wire guide via fulcrum 304 (FIG. 6B). As elongate member 302 advances into the ductal system, the tether will also be advanced by virtue of its contact with fulcrum 304. Preferably, fulcrum 304 is advanced past stricture 608 so that the biliary stent can be pulled into place when advanced into the target anatomy. Once elongate member 302 is advanced to the desired location, variable stiffness cable 306 may be engaged by manipulation of actuator 314, thereby causing stiffening of the elongate member 302 (FIGS. 3A and 6B). Stiffening anchors the elongate member in position and provides rigidity which can prevent buckling during delivery of device 120.

Next, the biliary stent may be coupled to the tether at the proximal portion of the endoscope. Preferably, the stent is loaded into and delivered via a delivery catheter that is configured to couple to the tether. The delivery catheter, as device 120, includes a coupling element 122 for coupling to the tether, and preferably includes a stiffening element or a partially rigid portion so that the catheter can be pushed from its proximal end 124. Pushing the stent or the delivery catheter can reduce tension on the tether during introduction and may reduce the incidence of mucosal trauma. Once coupled, device 120 may be advanced alongside the endoscope by pulling the tether out in the proximal direction at port 114.

Figure 6C:
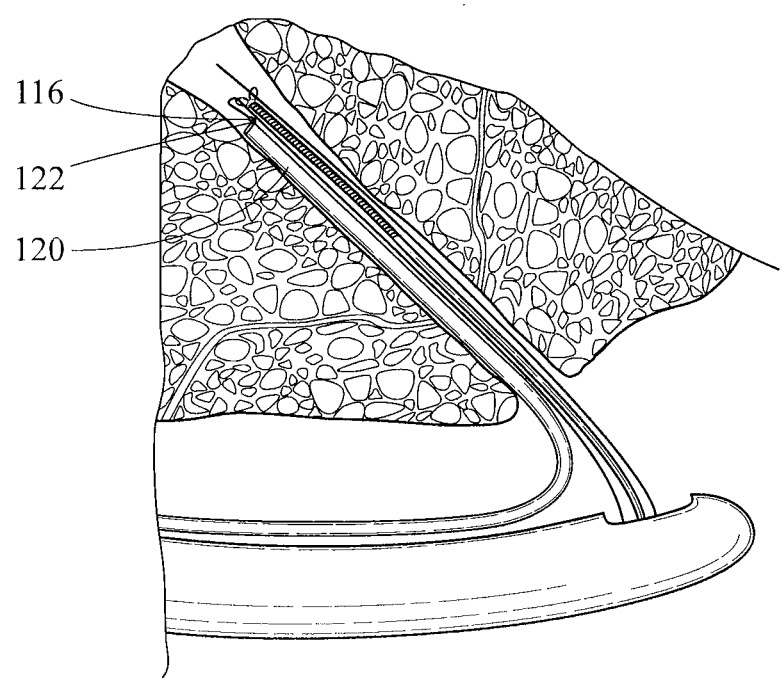
Figure 6D:
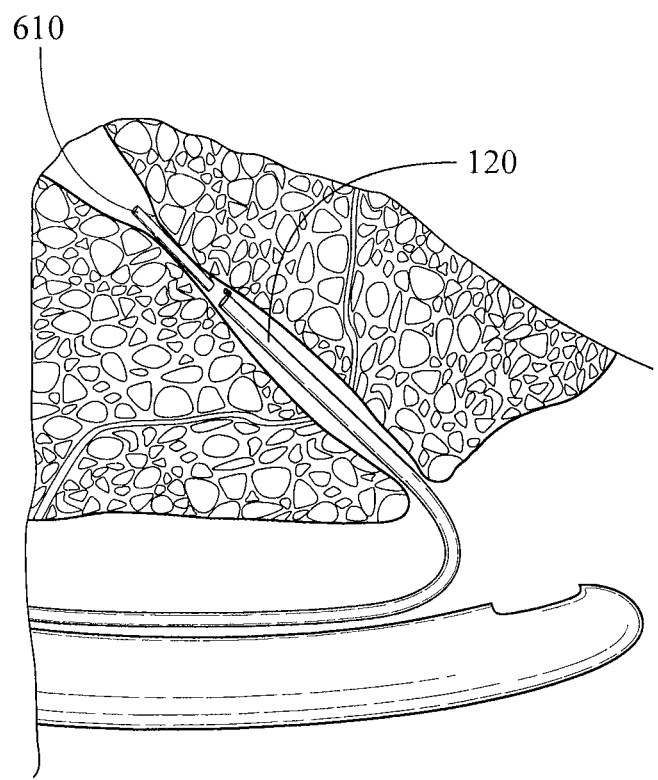

Upon reaching the distal portion of the endoscope, the delivery catheter may be advanced along elongate member 302 of guiding device 300 by continuing to push from the proximal end while pulling with tether 104. Preferably, the delivery catheter is advanced to distal portion 310, and thus, the target anatomy (FIG. 6C). Once the delivery catheter reaches the target site (i.e., the stricture), it may then be decoupled from the tether. For example, the delivery catheter may be held at the proximal end while the tether is pulled back at port 114 with sufficient force to detach coupling element 116 from coupling element 122, thereby decoupling the delivery catheter from the tether. The tether may then be pulled out of the ductal system and back into the endoscope working channel 110. The guiding member 300 and subsequently the wire guide 350 may be advanced out of the ductal system and back into the endoscope. Next, the biliary stent 610 may be delivered to the site of the stricture 608 by pushing the stent out of the delivery catheter using an internal pushing catheter (FIG. 6D). The delivery catheter may then be removed from the patient anatomy. The skilled artisan will appreciate that the steps of accessing, delivering, decoupling, and removal of devices from the target anatomy may be varied as necessary. For example, if additional procedures are to be performed using the wire guide, it may be preferable to only partially retract the wire guide from the bile duct.

Figure 6E:
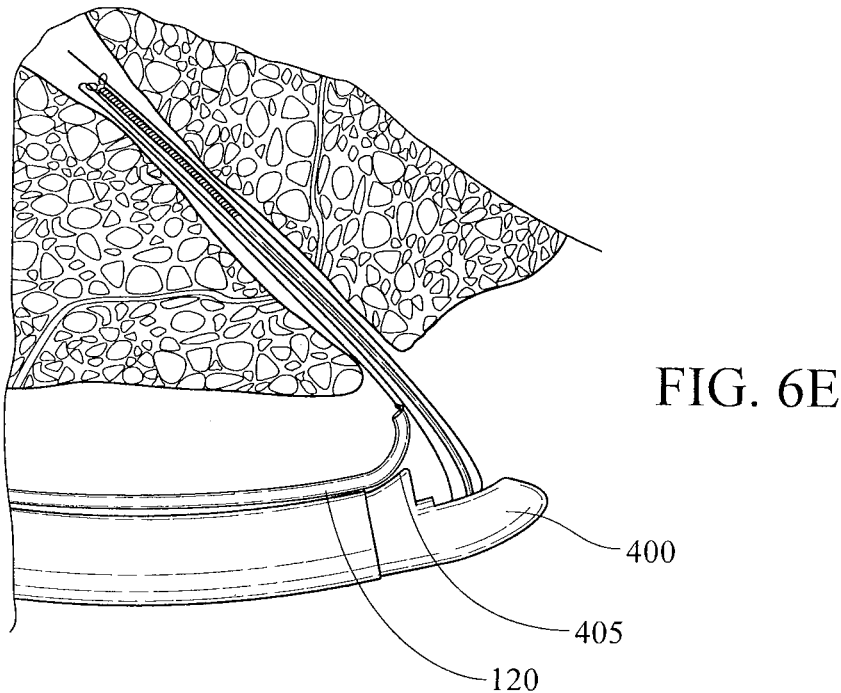

In alternative embodiments of the above ERCP procedure, the endoscope cap 400 and/or the endoscope sheath 500 may be used with the advancing system to facilitate delivery of the device 120 to the stricture 608. FIG. 6E shows endoscope cap 400 disposed on the distal end of endoscope 102. Ramp 405 facilitates angular motion of the delivery catheter (device 120) as it is delivered to the distal portion of the endoscope.

Figure 6F:
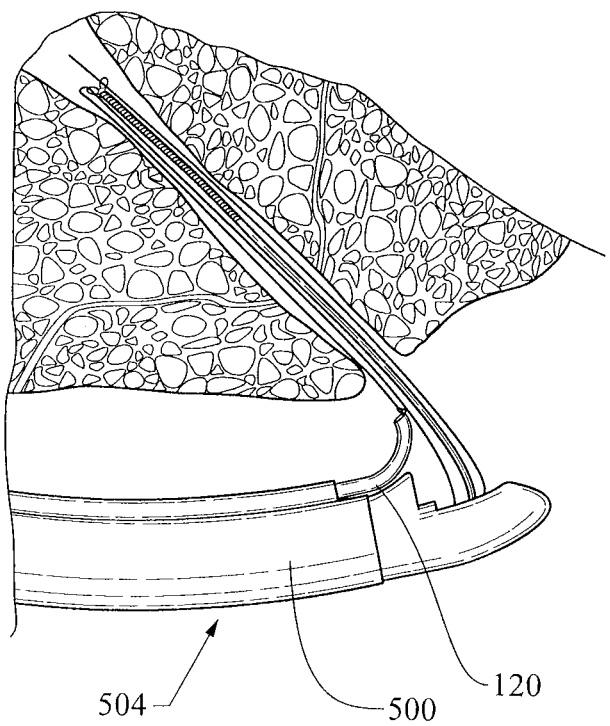
Figure 6G:
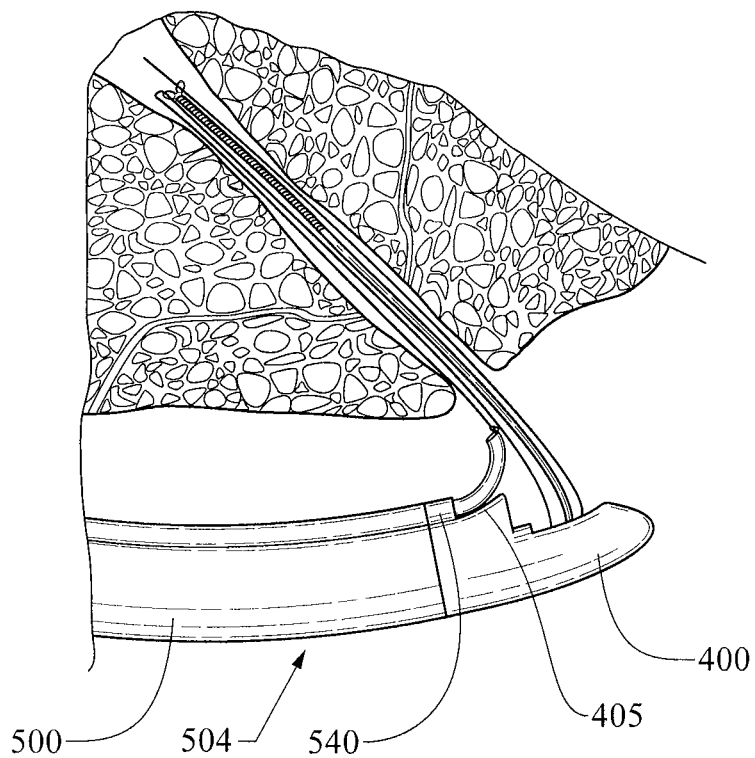

FIG. 6F shows the endoscope having an endoscope sheath 500. The delivery catheter is advanced to the distal portion of the endoscope through lumen 520 of the sheath. FIG. 6G shows endoscope cap 400 and sheath 500 used in combination. In this embodiment, the cap includes a coupling member 540 that couples to lumen 520. The cap also includes a lumen 546 (not shown) that is aligned with ramp 405 such that once device 120 exits the sheath lumen and lumen 546, the device will intersect ramp 405 and be deflected thereby.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

The invention claimed is:

1. An advancing system comprising:
   an endoscope having a proximal portion, a distal portion, a working channel extending from the proximal portion to the distal portion, an aperture disposed at the distal portion and in communication with the working channel, and a port disposed at the proximal portion and in communication with the working channel;
   a flexible tether comprising a first portion extending external the endoscope from the proximal portion of the endoscope to the aperture, the tether further comprising a second portion extending through the working channel from the aperture to the proximal portion of the endoscope, wherein the first portion of the tether comprises a coupling element configured to be coupled to a medical device and apply a pulling force thereto; and
   a guiding device configured to be movably advanced through the working channel of the endoscope and alongside the second portion of the tether, the guiding device comprising an elongate shaft having a shaft proximal portion and a shaft distal portion, the guiding device further comprising a fulcrum disposed at the shaft distal portion and configured to movably receive the tether there through at a location distal of and spaced apart from the distal portion of the endoscope.

2. The advancing system of claim 1, wherein the coupling element comprises a closed loop structure, releasable or breakable sutures, temporary or dissolvable bonds, adhesives, magnets, or a combination thereof.

3. The advancing system of claim 1, wherein the tether comprises a hydrophilic or lubricious coating.

4. The advancing system of claim 1, wherein the tether is selected from the group consisting of a wire, a strap, a thread, or a suture.

5. The advancing system of claim 1 further comprising at least one guide ring disposed on an external surface of the endoscope and configured to guide the tether alongside the endoscope from the proximal portion to the distal portion.

6. The advancing system of claim 1,
   wherein the elongate shaft comprises a variable stiffness cable comprising:
      a helical spring extending from the shaft proximal portion to the shaft distal portion;
      a wire extending through the spring, the wire operatively connected to the spring at the shaft distal portion; and
      an actuator operatively connected to the wire and disposed proximal to the shaft proximal portion, wherein actuation of the actuator causes the spring to be compressed.

7. The advancing system of claim 1, wherein the fulcrum consists of one of a single looped structure, a double looped structure, or a cylindrical structure.

8. The advancing system of claim 1, wherein the elongate shaft includes a hydrophilic or lubricious coating.

9. An advancing system configured for use with an endoscope having a proximal portion, a distal portion, a working channel extending from the proximal portion to the distal portion, an aperture disposed at the distal portion and in communication with the working channel, and a port disposed at the proximal portion and in communication with the working channel, the advancing system comprising:
 a flexible tether comprising a first portion extending external the endoscope from the proximal portion of the endoscope to the aperture, the first portion of the tether comprising a coupling element configured to be coupled to a medical device and apply a pulling force thereto, the tether further comprising a second portion extending through the working channel from the aperture to the proximal portion of the endoscope; and
 a guiding device configured to be movably advanced through the working channel of the endoscope and alongside of the second portion of the tether, the guiding device comprising:
  an elongate shaft having a shaft proximal portion and a shaft distal portion;
  a fulcrum disposed at the shaft distal portion and configured to movably receive the tether there through;
  a variable stiffness cable disposed through the elongate shaft, comprising a helical spring extending from the shaft proximal portion to the shaft distal portion, and a wire extending through the spring, the wire operatively connected to the spring at the shaft distal portion; and
  an actuator operatively connected to the wire and disposed proximal to the shaft proximal portion.

10. The advancing system of claim 9, wherein the fulcrum comprises one of a single looped structure, a double looped structure, or a cylindrical structure.

11. The advancing system of claim 9, wherein the elongate shaft comprises a first aperture at the shaft distal portion and in communication with a second aperture disposed proximal to the first aperture and located at the shaft distal portion.

12. The advancing system of claim 9, wherein at least a portion of the elongate shaft comprises a hydrophilic or lubricious material.

13. The advancing system of claim 9, wherein the fulcrum has a diameter ranging from about 1 mm to about 3 mm.

14. The advancing system of claim 9, wherein the elongate shaft includes a hydrophilic or lubricious coating.

15. The advancing system of claim 9, wherein the tether is selected from the group consisting of a wire, a strap, a thread, or a suture.

16. The advancing system of claim 9, wherein the tether comprises a hydrophilic or lubricious coating.

\* \* \* \* \*